US010806809B2

(12) United States Patent
Ukawa et al.

(10) Patent No.: US 10,806,809 B2
(45) Date of Patent: *Oct. 20, 2020

(54) LIGHT-EMITTING DEVICE

(71) Applicant: NICHIA CORPORATION, Anan-shi (JP)

(72) Inventors: Hiroaki Ukawa, Itano-gun (JP); Ryuichi Nakagami, Anan (JP)

(73) Assignee: NICHIA CORPORATION, Anan-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/668,153

(22) Filed: Oct. 30, 2019

(65) Prior Publication Data

US 2020/0061222 A1 Feb. 27, 2020

Related U.S. Application Data

(63) Continuation of application No. 16/142,860, filed on Sep. 26, 2018, now Pat. No. 10,493,175.

(30) Foreign Application Priority Data

Sep. 28, 2017 (JP) .................................. 2017-187604

(51) Int. Cl.
*A61L 2/08* (2006.01)
*H01L 33/50* (2010.01)
(Continued)

(52) U.S. Cl.
CPC .............. *A61L 2/084* (2013.01); *A61L 2/26* (2013.01); *A61L 9/18* (2013.01); *C09K 11/0883* (2013.01);
(Continued)

(58) Field of Classification Search
CPC ... A61L 2/084; A61L 9/18; A61L 2/26; A61L 2202/11; F21K 9/00; C09K 11/7774;
(Continued)

(56) References Cited

U.S. PATENT DOCUMENTS 10,026,876 B2 7/2018 Hosokawa et al.
2003/0006469 A1 1/2003 Ellens et al.
(Continued)

FOREIGN PATENT DOCUMENTS

JP 2008034188 A 2/2008
JP 2009289957 A 12/2009
(Continued)

*Primary Examiner* — David P Porta
*Assistant Examiner* — Gisselle M Gutierrez
(74) *Attorney, Agent, or Firm* — Hunton Andrews Kurth LLP

(57) ABSTRACT

A light-emitting device includes a light-emitting element with a peak emission wavelength in a range of 400 nm to 410 nm and a fluorescent member that contains a first phosphor with a peak emission wavelength in a range of 440 nm to 470 nm containing a Eu-activated alkaline-earth phosphate that contains Cl in a composition, a second phosphor with a peak emission wavelength in a range of 500 nm to 530 nm containing a Eu-activated halogen-containing alkaline-earth silicate, a third phosphor with a peak emission wavelength in a range of 530 nm to 600 nm containing a Ce-activated rare-earth aluminate, and a fourth phosphor with a peak emission wavelength in a range of 600 nm to 660 nm containing a Eu-activated silicon nitride containing Al and at least one of Sr and Ca in a composition.

19 Claims, 5 Drawing Sheets

(51) Int. Cl.
*H01L 33/60* (2010.01)
*H01L 33/64* (2010.01)
*C09K 11/77* (2006.01)
*C09K 11/08* (2006.01)
*A61L 2/26* (2006.01)
*A61L 9/18* (2006.01)
*F21K 9/00* (2016.01)
*H01L 33/62* (2010.01)

(52) U.S. Cl.
CPC ...... *C09K 11/7734* (2013.01); *C09K 11/7739* (2013.01); *C09K 11/7774* (2013.01); *F21K 9/00* (2013.01); *H01L 33/504* (2013.01); *H01L 33/60* (2013.01); *H01L 33/647* (2013.01); *A61L 2202/11* (2013.01); *H01L 33/62* (2013.01)

(58) Field of Classification Search
CPC ............ C09K 11/7734; C09K 11/7739; C09K 11/0883; H01L 33/647; H01L 33/60; H01L 33/504; H01L 33/62

USPC ...................................................... 250/458.1
See application file for complete search history.

(56) References Cited

U.S. PATENT DOCUMENTS

| | | |
|---|---|---|
| 2003/0146690 A1 | 8/2003 | Ellens et al. |
| 2005/0104503 A1 | 5/2005 | Ellens et al. |
| 2006/0103291 A1 | 5/2006 | Ellens et al. |
| 2016/0276550 A1 | 9/2016 | David et al. |
| 2017/0179347 A1 | 6/2017 | Asai |

FOREIGN PATENT DOCUMENTS

| | | |
|---|---|---|
| JP | 2010207278 A | 9/2010 |
| JP | 2013536583 A | 9/2013 |
| JP | 2016111190 A | 6/2016 |
| JP | 2017011153 A | 1/2017 |
| JP | 2017138534 A | 8/2017 |
| WO | 2001093341 A1 | 12/2001 |

LIGHT-EMITTING DEVICE

CROSS-REFERENCE TO RELATED APPLICATION

This is a continuation application of U.S. patent application Ser. No. 16/142,860 filed Sep. 26, 2018, which claims priority to Japanese Patent Application No. 2017-187604, filed on Sep. 28, 2017, the disclosure of which is hereby incorporated by reference in its entirety.

BACKGROUND

The disclosure of the present disclosure relates to a light-emitting device.

Examples of light-emitting devices that employ light-emitting diodes (hereinafter also referred to as "LEDs") to emit white light include a light-emitting device employing a combination of a LED capable of emitting blue light and a phosphor capable of emitting yellow light. This light-emitting device emits white light as a mixture of the colors of blue light emitted from the LED and yellow light emitted from the phosphor excited by the blue light. Such a light-emitting device shows high emission intensity and efficiency in the visible region but does not provide sufficient emission intensity in the blue-green and red regions in some cases. Hence, how the color of an irradiated object looks (hereinafter referred to as "color rendering properties") has room for further improvement.

The method of specifying color rendering properties of light sources defined by JIS Z 8726 includes numerically calculating the color difference $\Delta E_i$ (where i is an integer from 1 to 15) between measurements of a test color (R1 to R15), which has predetermined reflectance properties, under a test light source and the reference light source to calculate a color rendering index. The upper limit of the color rendering index Ri (where i is an integer from 1 to 15) is 100. In other words, the smaller the color difference between the test light source and the reference light source having the color temperature corresponding to the test light source is, the higher and closer to 100 the color rendering index is. Among color rendering indices, the average value of R1 to R8 is called the general color rendering index (hereinafter also referred to as Ra), and special color rendering indices are obtained by using R9 to R15. For the special color rendering indices, R9 is defined as red, R10 as yellow, R11 as green, R12 as blue, R13 as the skin color of Westerners, R14 as the color of tree leaves, and R15 as the skin color of Japanese.

For example, WO2001/093341 discloses a light-emitting device including an light emitting element and two types of phosphors that emit green to yellow light, such as a chlorosilicate phosphor and a garnet phosphor containing Y or Tb, in order to improve the color rendering properties of the light source. Also, Japanese Unexamined Patent Application Publication No. 2008-034188 proposes a light-emitting device including a phosphor that emits red light in addition to a phosphor that emits green to yellow light in order to further improve the color rendering properties.

In addition, Japanese Unexamined Patent Application Publication No. 2010-207278 proposes a surface sterilization method that achieves sterilization without exerting harmful effects on the human body by radiating light (near-ultraviolet light) with a maximum intensity at 400 nm to 410 nm.

The present disclosure has an object to provide a light-emitting device that has good color rendering properties and can alleviate the proliferation of germs.

SUMMARY

A light-emitting device according to the present disclosure includes a light-emitting element with a peak emission wavelength in a range of 400 nm to 410 nm and a fluorescent member that contains a first phosphor with a peak emission wavelength in a range of 440 nm to 470 nm containing a Eu-activated alkaline-earth phosphate containing Cl in a composition, a second phosphor with a peak emission wavelength in a range of 500 nm to 530 nm containing a Eu-activated halogen-containing alkaline-earth silicate, a third phosphor with a peak emission wavelength in a range of 530 nm to 600 nm containing a Ce-activated rare-earth aluminate, and a fourth phosphor with a peak emission wavelength in a range of 600 nm to 660 nm containing a Eu-activated silicon nitride containing Al and at least one of Sr and Ca in a composition.

An embodiment of the present disclosure can provide a light-emitting device that has good color rendering properties and can alleviate the proliferation of germs.

DETAILED DESCRIPTION

Figure 1:
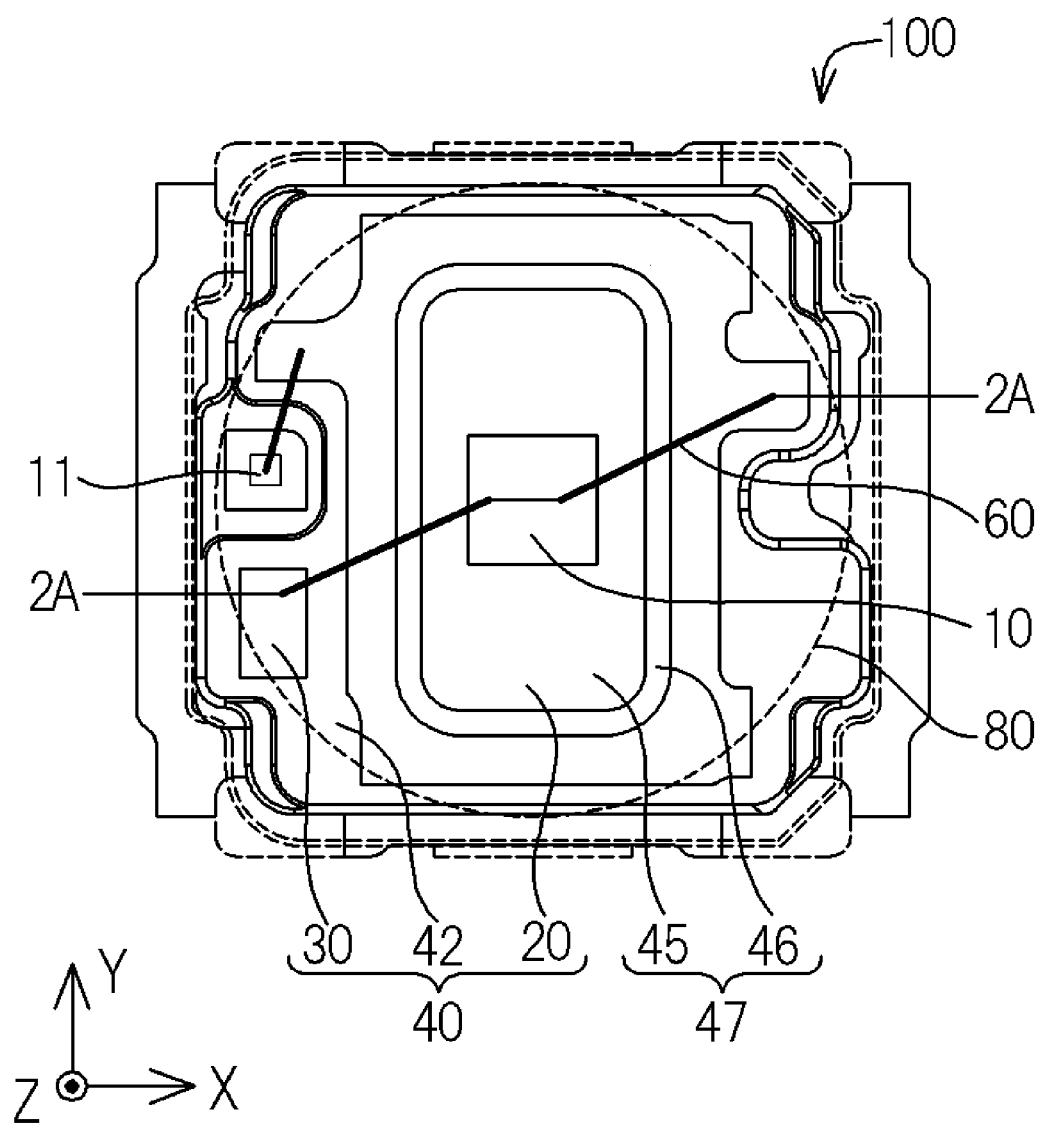
FIG. 1 is a schematic top view of a light-emitting device according to a first embodiment.
Figure 2:
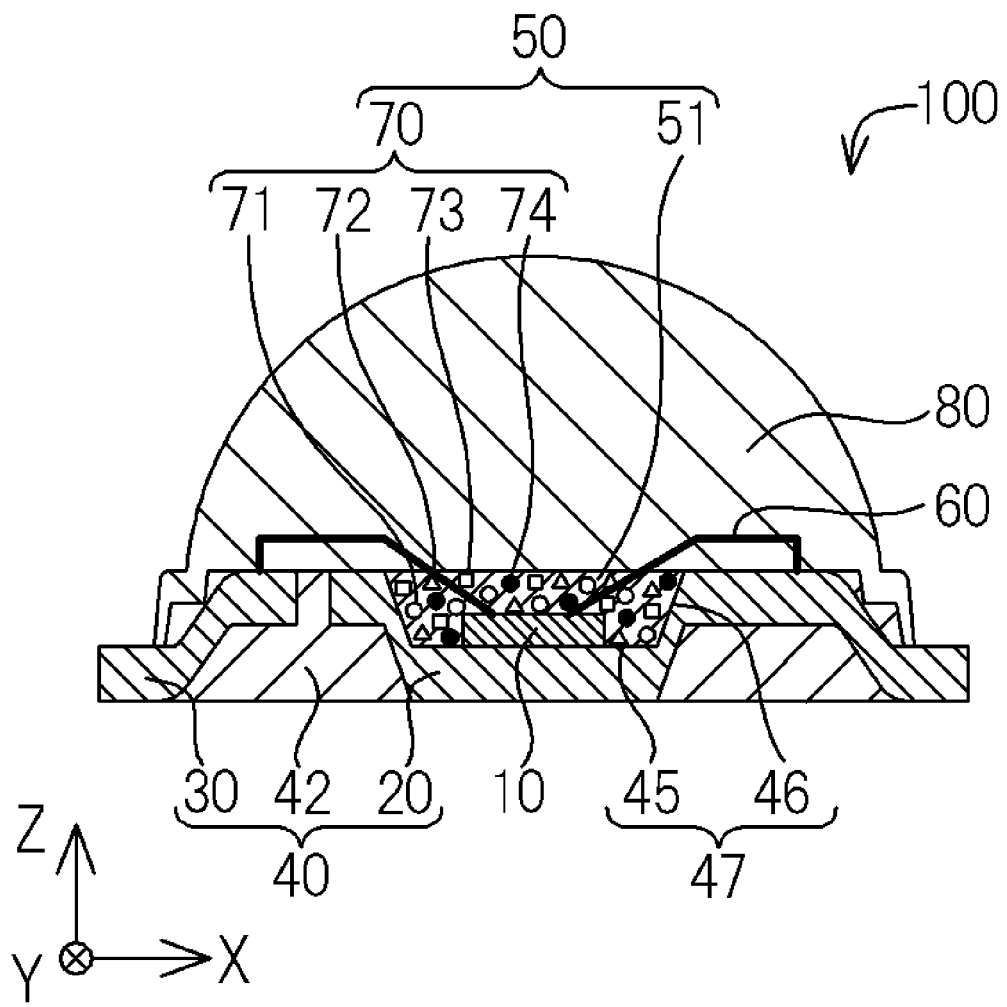
FIG. 2 is a schematic end view of the light-emitting device taken along the line 2A-2A in FIG. 1.

The following describes an embodiment of the present disclosure. The embodiment below is an example of a light-emitting device intended to embody the technical concept of the present disclosure and does not limit the present invention to the light-emitting device below. In the present specification, JIS Z 8110 is applied to the relations between color names and chromaticity coordinates, the relations between wavelength regions of light and color names of monochromatic lights, and the like. In the case where a composite contains a plurality of substances corresponding to each element, the content of the element in the composite means the total amount of the substances in the composite unless otherwise noted.

Light-Emitting Device

A light-emitting device 100 according to an embodiment of the present disclosure will be described on the basis of FIG. 1 to FIG. 7. The light-emitting device 100 includes a fluorescent member 50 and a light-emitting element 10 with a peak emission wavelength in the range of 400 nm to 410 nm. The fluorescent member 50 configured as phosphors 70 contains at least four types of phosphors including a first phosphor 71, a second phosphor 72, a third phosphor 73, and a fourth phosphor 74. The first phosphor 71 has a peak emission wavelength in the range of 440 nm to 470 nm, and contains a Eu-activated alkaline-earth phosphate containing Cl in its composition. The second phosphor 72 has a peak emission wavelength in the range of 500 nm to 530 nm, and contains a Eu-activated halogen-containing alkaline-earth silicate. The third phosphor 73 has a peak emission wavelength in the range of 530 nm to 600 nm, and contains a Ce-activated rare-earth aluminate. The fourth phosphor 74 has a peak emission wavelength in the range of 600 nm to 660 nm, and contains a Eu-activated silicon nitride containing Al and at least one of Sr and Ca in its composition.

The light-emitting device 100 includes at least four specific phosphors and the light-emitting element 10 having a specific peak emission wavelength, therefore it is possible for the emission spectrum of the light-emitting device 100 to be close to the spectrum of the reference light source throughout an extremely broad region from the short wavelength to the long wavelength in the visible region involved in the calculation of the color rendering indices. Good color rendering properties can be thus obtained. Employing the light-emitting element 10 having a peak emission wavelength in the range of 400 nm to 410 nm can alleviate the proliferation of germs. Sterilization or removal of germs can also be achieved by increasing the emission intensity of the light-emitting element 10. In addition, the light-emitting element 10 having a peak emission wavelength in the range of 400 nm to 410 nm can achieve the light-emitting device having less effects on the human body and being safer than in the case where the light-emitting element has a peak emission wavelength in the ultraviolet region, which includes wavelengths shorter than 380 nm. In the case where the light-emitting element has a peak emission wavelength in the range of 400 nm to 410 nm, it is easy to judge whether the light is being emitted, and less likely to influence on the chromaticity, whereas it is difficult to visually recognize ultraviolet light with wavelengths shorter than 380 nm and to judge whether the light is being emitted.

The International Commission on Illumination (CIE) has announced a guide on color rendering properties that should be provided by fluorescent lamps in terms of the average color rendering index Ra in year of 1986. According to the guide, preferable general color rendering indices Ra depending on the places of use are 60 to less than 80 for factories where general work is carried out, 80 to less than 90 for houses, hotels, restaurants, stores, offices, schools, hospitals, and factories where precision work is carried out, and 90 or more for places where high color rendering properties are necessitated, such as places where clinical examinations are carried out and museums.

The light-emitting device 100 according to the present embodiment has an Ra of, for example, preferably 80 or more, more preferably 90 or more, further preferably 95 or more. Each of the special color rendering indices R9 to R15 of the light-emitting device 100 is, for example, preferably at least 50, more preferably at least 70, further preferably at least 90. In particular, the R12 is, for example, preferably at least 50, more preferably at least 70, further preferably at least 90. The sum total (hereinafter also referred to as Rt) of the special color rendering indices R9 to R15 is, for example, preferably at least 550, more preferably at least 600, further preferably at least 650.

The light-emitting device 100 emits light with a mixed color of the light emitted from the light-emitting element 10 and the colors of fluorescence emitted from the first phosphor 71, the second phosphor 72, the third phosphor 73, and the fourth phosphor 74. For example, the mixed light may have chromaticity coordinates specified in CIE 1931 in the range of x=0.00 to 0.60 and y=0.00 to 0.50 or in the range of x=0.25 to 0.50 and y=0.25 to 0.50. The correlated color temperature of light emitted from the light-emitting device 100 is, for example, 2000 K or higher, or 2500 K or higher. Also, the correlated color temperature is 7500 K or lower, or 7000 K or lower.

The light-emitting device 100 includes the light-emitting element 10 and a base member 40 on which the light-emitting element 10 is mounted. The light emitting element 10 is made of a gallium nitride compound semiconductor, and have a peak emission wavelength in the range of 400 nm to 410 nm. The base member 40 includes electrically-conductive members and an insulating supporting member. Examples of the electrically-conductive members include metal members constituting leads and wiring. For the supporting member, a known material, such as resins and ceramics, can be used.

The electrically-conductive members of the light-emitting device 100 include a first lead 20 and a second lead 30 made of metal. The insulating supporting member 42 is made of resin. One of the first lead 20 and the second lead 30 functions as an external-connecting terminal of a positive electrode, and the other one functions as an external-connecting terminal of a negative electrode. The light-emitting element 10 is mounted on the first lead 20. The light-emitting element is mounted on the first lead 20 made of metal, therefore, heat of the light-emitting element is transferred to the first lead made of metal. This can improve the heat dissipation of the light-emitting device. The first lead 20 preferably has a depressed portion 47 defined by lateral walls 46 and a bottom portion 45. When the light-emitting element is mounted on the bottom portion 45 of the first lead, the lateral walls 46 and/or the bottom portion 45 of the first lead reflect light emitted from the light-emitting element, thereby improving the light extraction efficiency of the light-emitting device.

The first lead 20 and/or the second lead 30 preferably protrude from lateral surfaces of the supporting member 42. The volume of the first lead 20 and/or the second lead 30 thus increases, thereby improving the heat dissipation. The surface opposite the bottom portion 45 of the first lead 20 is preferably exposed from the supporting member 42. This can increases the contact area between the substrate and the first lead 20 when the light-emitting device 100 is mounted on a substrate, thereby improving the heat dissipation of the light-emitting device.

The light-emitting element 10 includes a pair of positive and negative electrodes electrically connected respectively to the first lead 20 and the second lead 30 via wires 60. The light-emitting element 10 is covered with the fluorescent member 50. The phosphors 70 in the fluorescent member 50 convert wavelength of light emitted from the light-emitting element 10, and contains, for example, at least four types of phosphors including the first phosphor 71, the second phosphor 72, the third phosphor 73, and the fourth phosphor 74, and contains a resin portion 51.

The peak emission wavelength of the light-emitting element 10 is in the range of 400 nm to 410 nm. The light-emitting element 10 is used for an excitation light source, thus the light-emitting device 100 that emits light with a mixed color of light emitted from the light-emitting element 10 and fluorescence emitted from the phosphors 70 can be provided. The light-emitting element 10 has a peak emission wavelength in the range of 400 nm to 410 nm, whereby the proliferation of germs can be alleviated. Also, having the peak emission wavelength in the range of 400 nm to 410 nm exerts less influences on the human body than in the case where the light-emitting element has a peak emission wavelength in the ultraviolet region, which includes wavelengths shorter than 380 nm. In addition, having the peak emission wavelength in the range of 400 nm to 410 nm can alleviate deterioration of the resin materials and other materials caused by light is suppressed compared with the case where the light-emitting element has a peak emission wavelength in the ultraviolet region, which includes wavelengths shorter than 380 nm.

The amount of energy of the light-emitting device 100 per unit time in the range of 400 nm to 410 nm is preferably in the range of 10 mW to 60 mW, preferably 20 mW to 50 mW, more preferably 30 mW to 45 mW. Because the amount of energy of the light-emitting device 100 per unit time in the range of 400 nm to 410 nm is within the above range, the proliferation of germs can be alleviated, and the influences on the human body are reduced. Here, the electric power supplied to the light-emitting device is, for example, 0.4 W.

The half-width in the emission spectrum of the light-emitting element 10 can be, for example, 30 nm or less. A semiconductor light-emitting element such as an LED can preferably be used for the light-emitting element 10. Using a semiconductor light-emitting element for a light source can achieve a high-efficiency stable light-emitting device 100 that has high linearity of output relative to input and is resistant to mechanical shock.

Figure 3:
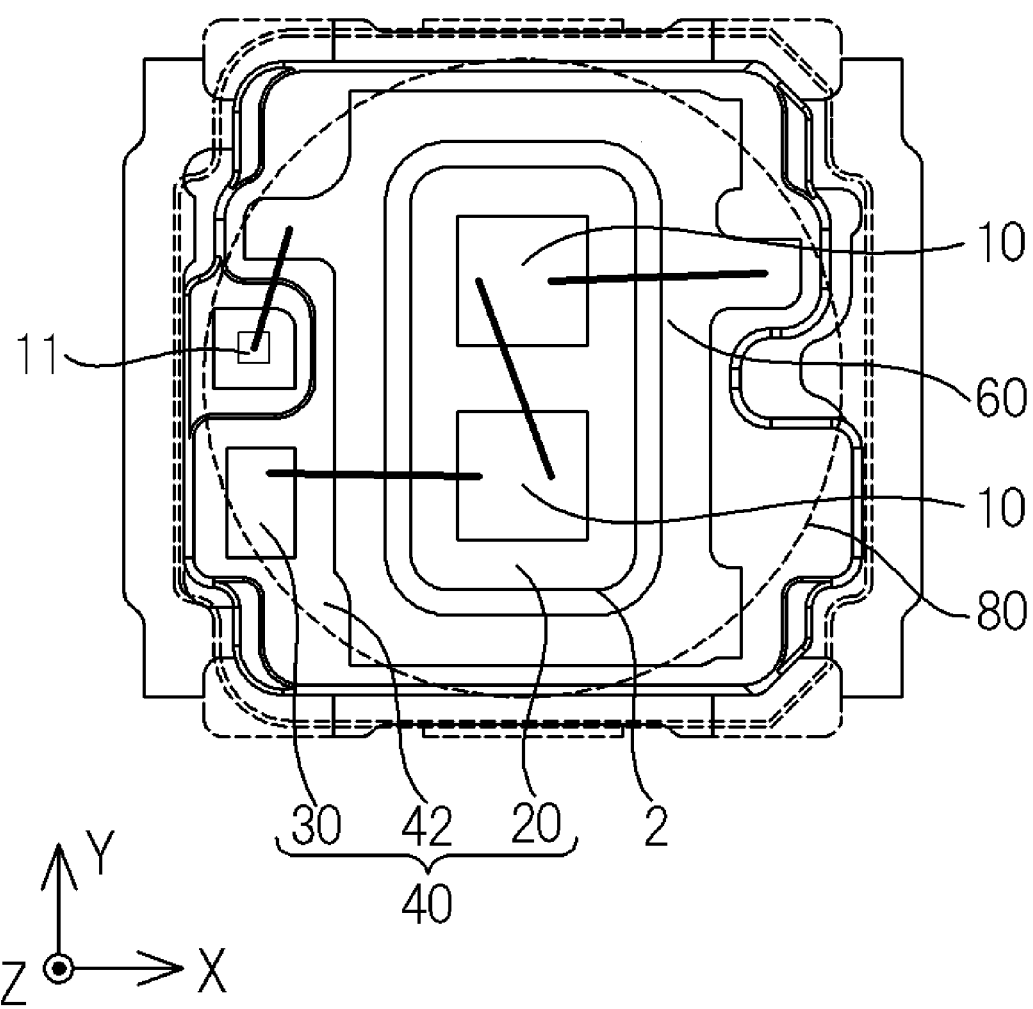
FIG. 3 is a schematic top view of a modification of the light-emitting device according to the first embodiment.

An example of the semiconductor light-emitting element is one that uses a nitride semiconductor $(In_XAl_YGa_{1-X-Y}N$, where X and Y satisfy $0 \leq X$, $0 \leq Y$, and $X+Y \leq 1$) which emit blue light. The light-emitting device 100 includes at least one light-emitting element 10. For example, the light-emitting device may include two or more light-emitting elements 10 as shown in FIG. 3. In the case where the light-emitting device includes two or more light-emitting elements, the light-emitting elements may have the same peak emission wavelength or different peak emission wavelengths.

The fluorescent member 50 can contain, for example, the phosphors 70 and the resin portion 51. The phosphors 70 in the fluorescent member 50 contains at least one type of first phosphor 71 that absorbs light emitted from the light-emitting element 10 and emits blue light, at least one type of second phosphor 72 that emits green light, at least one type of third phosphor 73 that emits green and/or yellow light, and at least one type of fourth phosphor 74 that emits red light. The compositions of the first phosphor 71, the second phosphor 72, the third phosphor 73, and the fourth phosphor 74 differ from one another. The properties such as the light emission efficiency and the color rendering properties of the light-emitting device 100 can be adjusted to desired ranges by appropriately selecting the ratio between the first phosphor 71, the second phosphor 72, the third phosphor 73, and the fourth phosphor 74.

The first phosphor 71 is a blue-light emitting phosphor that has a peak emission wavelength in the range of 440 nm to 470 nm and contains a Eu-activated alkaline-earth phosphate containing Cl in its composition. The first phosphor 71 preferably has, for example, the composition represented by Formula (1) below, more preferably the composition represented by Formula (1') below. The composition represented by Formula (1) contains at least one element selected from the group consisting of Ca, Sr and Ba. The composition represented by Formula (1) may contain Cl (without Br) or contain both Cl and Br. With such a composition, the light emission properties described below of the first phosphor 71 can be comparatively easily obtained.

Figure 4:
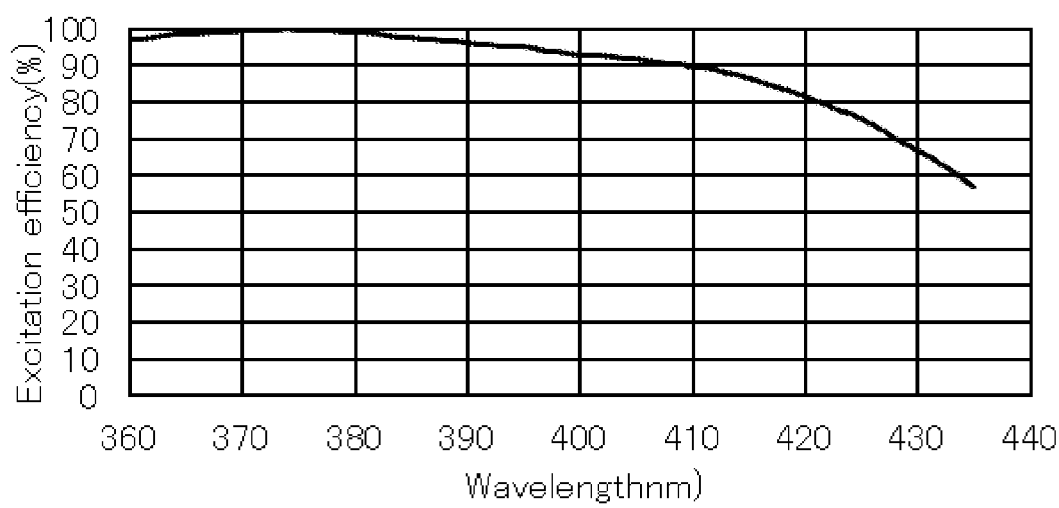
FIG. 4 is the excitation spectrum of a first phosphor (i.e., CCA) according to the present disclosure.

As shown in FIG. 4, the first phosphor 71 can have a high excitation efficiency in the range of 400 nm to 410 nm, which is the range of the peak emission wavelength of the light-emitting element 10. Hence, the first phosphor 71 can be efficiently excited. The peak emission wavelength of the first phosphor 71 is in the range of, for example, 440 nm to 470 nm, preferably 450 nm to 470 nm. Employing such a range reduces portions of the emission spectrum of the first phosphor 71 overlapping the emission spectrum of the light-emitting element 10 and the emission spectrum of the second phosphor 72. Thus the emission spectrum of the light-emitting device can becomes close to the emission spectrum of the reference light source, thereby further improving the color rendering properties of the light-emitting device 100.

The half-width in the emission spectrum of the first phosphor 71 is in the range of, for example, 29 nm to 49 nm, preferably 34 nm to 44 nm. With such a range of the half-width, the color purity is improved, and the emission spectrum can become close to the emission spectrum of the reference light source, thereby improving the color rendering properties of the light-emitting device 100.

In the case of a light-emitting device 100 that emits light with a correlated color temperature of 3000 K to 4000 K, the maximum emission intensity in the range of 440 nm to 470 nm is preferably 0.001 to 0.04 times as large as the maximum emission intensity in the range of 400 nm to 410 nm. When the maximum emission intensity in the range of 400 nm to 470 nm falls within the above range, the emission spectrum of the light-emitting device can become even closer to the emission spectrum of the reference light source, thereby further improving the color rendering properties.

In the case of the light-emitting device 100 that emits light with a correlated color temperature of 3000 K to 4000 K, the content of the first phosphor 71 relative to the total amount of the phosphors in the fluorescent member 50 is, for example, preferably in the range of 5 mass % to 30 mass %, more preferably 10 mass % to 25 mass %, further preferably 15 mass % to 25 mass %. When the content ratio falls within the above range, the emission spectrum of the light-emitting device can become even closer to the emission spectrum of the reference light source, thereby further improving the color rendering properties.

In the case of the light-emitting device 100 that emits light with a correlated color temperature of 3000 K to 4000 K, the value of the content ratio of the first phosphor 71 to the fourth phosphor 74 is, for example, preferably in the range of 0.2 to 1.2, more preferably 0.3 to 1. When the value of the content ratio falls within the above range, the emission spectrum of the light-emitting device 100 can become even closer to the emission spectrum of the reference light source, thereby further improving the color rendering properties.

The second phosphor 72 is a green-light emitting phosphor that has a peak emission wavelength in the range of 500 nm to 530 nm and contains a Eu-activated halogen-containing alkaline-earth silicate. The second phosphor 72 preferably has, for example, the composition represented by Formula (2) below, more preferably the composition represented by Formula (2') below. The composition represented by Formula (2) includes at least one element selected from the group consisting of Ca, Sr and Ba. The composition represented by Formula (2) also includes at least one element selected from the group consisting of F, Cl and Br. With such a composition, the light emission properties described below of the second phosphor 72 can be comparatively easily obtained.

$$(Ca,Sr,Ba)_8MgSi_4O_{16}(F,Cl,Br)_2:Eu \qquad (2)$$

$$Ca_8MgSi_4O_{16}Cl_2:Eu \qquad (2')$$

Figure 5:
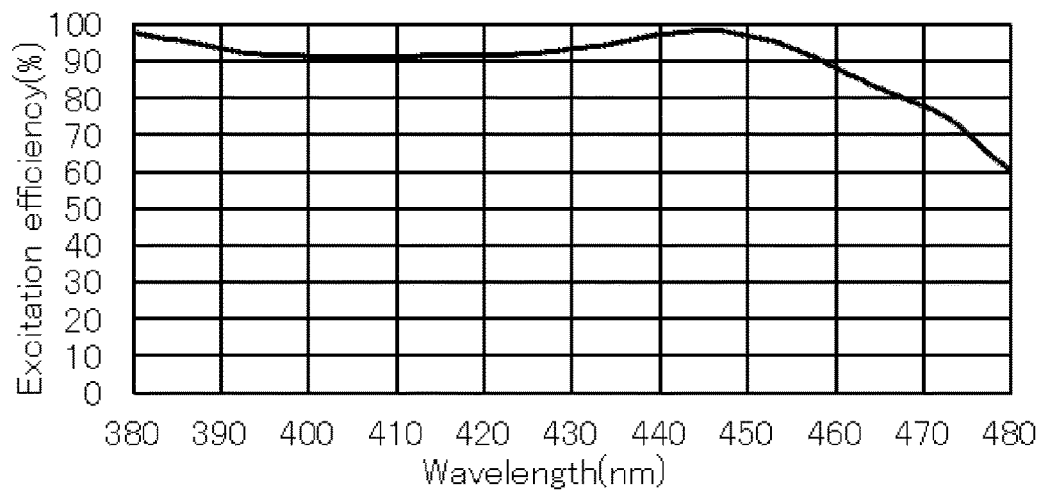
FIG. 5 is the excitation spectrum of a second phosphor (i.e., chlorosilicate).

As shown in FIG. 5, the second phosphor 72 can have a high excitation efficiency in the range of 400 nm to 410 nm, which is the range of the peak emission wavelength of the light-emitting element 10. Hence, the second phosphor 72 can be efficiently excited. The peak emission wavelength of the second phosphor 72 is in the range of, for example, 500 nm to 530 nm, preferably 505 nm to 525 nm. Employing such a range reduces portions of the emission spectrum of the second phosphor 72 overlapping the emission spectrum of the first phosphor 71 and the emission spectrum of the third phosphor 73. Thus the emission spectrum of the light-emitting device can become close to the emission spectrum of the reference light source, thereby further improving the color rendering properties of the light-emitting device 100.

The half-width in the emission spectrum of the second phosphor 72 is in the range of, for example, 52 nm to 72 nm, preferably 57 nm to 67 nm. With such a range of the half-width, the color purity is improved, and the emission spectrum can become close to the emission spectrum of the reference light source, thereby improving the color rendering properties of the light-emitting device 100.

In the case of the light-emitting device 100 that emits light with a correlated color temperature of 3000 K to 4000 K, the maximum emission intensity in the range of 500 nm to 530 nm is preferably 0.1 to 0.3 times as large as the maximum emission intensity in the range of 400 nm to 410 nm. When the maximum emission intensity in the range of 500 nm to 530 nm falls within the above range, the emission spectrum of the light-emitting device can become even closer to the emission spectrum of the reference light source, thereby further improving the color rendering properties.

In the case of the light-emitting device 100 that emits light with a correlated color temperature of 3000 K to 4000 K, the content of the second phosphor 72 relative to the total amount of the phosphors in the fluorescent member 50 is, for example, preferably in the range of 30 mass % to 55 mass %, more preferably 35 mass % to 50 mass %, further preferably 38 mass % to 48 mass %. When the content ratio falls within the above range, the emission spectrum of the light-emitting device can become even closer to the emission spectrum of the reference light source, thereby further improving the color rendering properties.

In the case of the light-emitting device 100 that emits light with a correlated color temperature of 3000 K to 4000 K, the content ratio of the second phosphor 72 to the fourth phosphor 74 is, for example, preferably in the range of 0.8 to 2.5, more preferably 1 to 2. When the value of the content ratio falls within the above range, the emission spectrum of the light-emitting device 100 can become even closer to the emission spectrum of the reference light source, thereby further improving the color rendering properties.

The third phosphor 73 is a green and/or yellow-light emitting phosphor that has a peak emission wavelength in the range of 530 nm to 600 nm and contains a Ce-activated rare-earth aluminate. The third phosphor 73 preferably has, for example, the composition represented by Formula (3) below, more preferably the composition represented by Formula (3') below. The composition represented by Formula (3) contains at least one element selected from the group consisting of Y, Lu and Gd. The composition represented by Formula (3) may contain Al (without Ga) or contain both Al and Ga. With such a composition, the light-emitting properties described below of the third phosphor 73 can be comparatively easily obtained.

$$(Y,Lu,Gd)_3(Al,Ga)_5O_{12}:Ce \qquad (3)$$

$$Y_3Al_5O_{12}:Ce \qquad (3')$$

Figure 6:
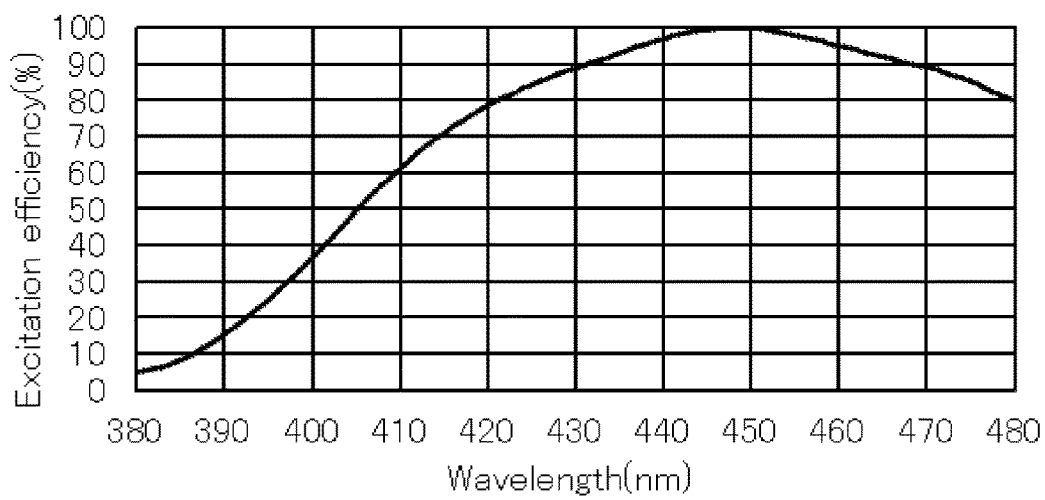
FIG. 6 is the excitation spectrum of a third phosphor (i.e., YAG) according to the present disclosure.

As shown in FIG. 6, the excitation efficiency of the third phosphor 73 is lower in the range of 400 nm to 410 nm, which is the range of the peak emission wavelength of the light-emitting element 10, than in the range of 440 nm to 470 nm. Because the light-emitting device 100 contains the first phosphor that has a peak emission wavelength in the range of 440 nm to 470 nm, the third phosphor 73 can efficiently excite light excited by the first phosphor. In other words, because the light-emitting device 100 contains the first phosphor and the third phosphor, the third phosphor can be efficiently excited. The peak emission wavelength of the third phosphor 73 is in the range of, for example, 530 nm to 600 nm, preferably 530 nm to 560 nm. Employing such a range reduces portions of the emission spectrum of the third phosphor 73 overlapping the emission spectrum of the second phosphor 72 and the emission spectrum of the fourth phosphor 74 in the emission spectrum of the light-emitting device 100. Thus the emission spectrum of the light-emitting device can become close to the emission spectrum of the reference light source, thereby further improving the color rendering properties of the light-emitting device 100.

The half-width in the emission spectrum of the third phosphor 73 is in the range of, for example, 95 nm to 115 nm, preferably 100 nm to 110 nm. With such a range of the half-width, the color purity is improved, and the emission spectrum can become close to the emission spectrum of the reference light source, thereby further improving the color rendering properties of the light-emitting device 100.

In the case of the light-emitting device 100 that emits light with a correlated color temperature of 3000 K to 4000 K, the content of the third phosphor 73 relative to the total amount of the phosphors in the fluorescent member 50 is, for example, preferably in the range of 5 mass % to 35 mass %, more preferably 10 mass % to 30 mass %, further preferably 13 mass % to 25 mass %. When the content ratio falls within the above range, the emission spectrum of the light-emitting device can become even closer to the emission spectrum of the reference light source, thereby further improving the color rendering properties.

In the case of the light-emitting device 100 that emits light with a correlated color temperature of 3000 K to 4000 K, the content ratio of the third phosphor 73 to the fourth phosphor 74 is, for example, preferably in the range of 0.4 to 2.5, more preferably 0.6 to 2. When the value of the content ratio falls within the above range, the emission spectrum of the light-emitting device 100 can become even closer to the emission spectrum of the reference light source, thereby further improving the color rendering properties.

The fourth phosphor 74 is a red-light emitting phosphor that has a peak emission wavelength in the range of 600 nm to 660 nm and contains a Eu-activated silicon nitride containing Al and at least one of Sr and Ca in its composition. The fourth phosphor 74 preferably has, for example, the composition represented by Formula (4) below. With such a composition, the light-emitting properties described below of the fourth phosphor 74 can be comparatively easily obtained.

(Sr,Ca)AlSiN$_3$:Eu    (4)

In the case where the fourth phosphor 74 has the composition represented by Formula (4), the fourth phosphor 74 contains at least one selected from the group consisting of Sr and Ca. Preferably, both Sr and Ca are contained. More preferably, the content of Sr relative to the total amount of Sr and Ca contained in the composition represented by Formula (4) is 0.8 mol % or more. With such a composition, the peak emission wavelength of the fourth phosphor 74 falls within a desired range.

Figure 7:
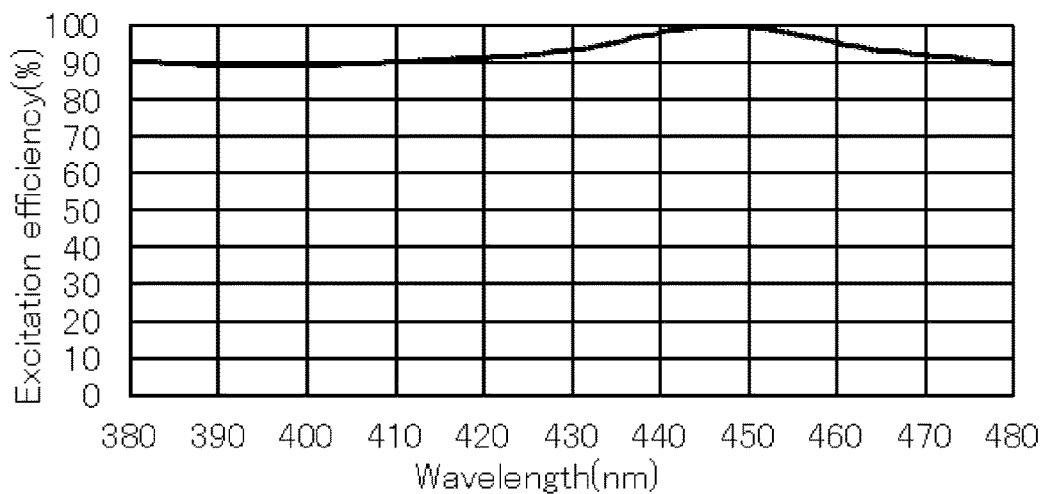
FIG. 7 is the excitation spectrum of a fourth phosphor (i.e., SCASN) according to the present disclosure.

As shown in FIG. 7, the fourth phosphor 74 can have a high excitation efficiency in the range of 400 nm to 410 nm, which is the range of the peak emission wavelength of the light-emitting element 10. Hence, the fourth phosphor 74 can be efficiently excited. The peak emission wavelength of the fourth phosphor 74 is in the range of, for example, 600 nm to 660 nm, preferably 620 nm to 660 nm. Employing such a range reduces portions of the emission spectrum of the fourth phosphor 74 overlapping the emission spectrum of the third phosphor 73 in the emission spectrum of the light-emitting device 100. Thus the emission spectrum of the light-emitting device can become close to the emission spectrum of the reference light source, thereby further improving the color rendering properties of the light-emitting device 100.

The half-width in the emission spectrum of the fourth phosphor 74 is in the range of, for example, 80 nm to 100 nm, preferably 85 nm to 95 nm. With such a range of the half-width, the color purity is improved, and the emission spectrum can become close to the emission spectrum of the reference light source, thereby further improving the color rendering properties of the light-emitting device 100.

In the case of the light-emitting device 100 that emits light with a correlated color temperature of 3000 K to 4000 K, the maximum emission intensity in the range of 600 nm to 660 nm is preferably 0.15 to 0.4 times as large as the maximum emission intensity in the range of 400 nm to 410 nm. When the maximum emission intensity in the range of 600 nm to 660 nm falls within the above range, the emission spectrum of the light-emitting device can become even closer to the emission spectrum of the reference light source, thereby further improving the color rendering properties.

In the case of the light-emitting device 100 that emits light with a correlated color temperature of 3000 K to 4000 K, the content of the fourth phosphor 74 relative to the total amount of the phosphors in the fluorescent member 50 is, for example, preferably in the range of 15 mass % to 45 mass %, more preferably 20 mass % to 40 mass %, further preferably 25 mass % to 35 mass %. When the content ratio falls within the above range, the emission spectrum of the light-emitting device can become even closer to the emission spectrum of the reference light source, thereby further improving the color rendering properties.

In the case of the light-emitting device 100 that emits light with a correlated color temperature of 3000 K to 4000 K, the maximum emission intensity in the wavelength range of 600 nm to 660 nm is preferably 1.5 to 10 times, more preferably 1.5 to 6 times, as large as the maximum emission intensity in the wavelength range of 440 nm to 470 nm. When the emission intensity falls within the above range, the emission spectrum of the light-emitting device can become even closer to the emission spectrum of the reference light source, thereby further improving the color rendering properties.

In the case of the light-emitting device 100 that emits light with a correlated color temperature of 3000 K to 4000 K, the maximum emission intensity in the wavelength range of 600 nm to 660 nm is preferably 1 to 2 times as large as the maximum emission intensity in the wavelength range of 500 nm to 530 nm. When the emission intensity falls within the above range, the emission spectrum of the light-emitting device can become even closer to the emission spectrum of the reference light source, thereby further improving the color rendering properties.

Particles of the first phosphor 71, particles of the second phosphor 72, particles of the third phosphor 73, and particles of the fourth phosphor 74 each have a size preferably in the range of 5 μm to 50 μm, more preferably 5 μm to 40 μm, more preferably 5 μm to 35 μm. Employing phosphors having the particle sizes in the above ranges or smaller are unlikely to cause clogging of the nozzle, when the fluorescent member is formed by discharging an uncured fluorescent member from a nozzle in the manufacture of the light-emitting device. Also, Employing phosphors having the particle sizes having in the above ranges or larger, the phosphors are unlikely to scatter light emitted from the light-emitting element. This can alleviate absorption of part of scattered light by the light-emitting element and the phosphors, thereby improving the light extraction efficiency of the light-emitting device.

In the present specification, the particle size means a median diameter (based on the volume) calculated from a particle size distribution measured with Coulter Multisizer II (manufactured by Beckman Coulter, Inc.) by the electric resistance method. The electric resistance method utilizes the correlation between the electric resistance and the particle size when dispersed powder passes through the gap between electrodes. Hence, when particles aggregate so strongly that it is difficult to disperse the particles in the form of primary particles, the particle size of aggregated secondary particles is measured.

The fluorescent member 50 may contain phosphors other than the first to fourth phosphors 71 to 74 as appropriate. Examples of the other phosphors include Ca$_3$Sc$_2$Si$_3$O$_{12}$:Ce, CaSc$_2$O$_4$:Ce, (La,Y)$_3$Si$_6$N$_{11}$:Ce, (Ca,Sr,Ba)$_3$Si$_6$O$_9$N$_4$:Eu, (Ca,Sr,Ba)$_3$Si$_6$O$_{12}$N$_2$:Eu, (Ba,Sr,Ca)Si$_2$O$_2$N$_2$:Eu, (Ca,Sr,Ba)$_2$Si$_5$N$_8$:Eu, (Ca,Sr,Ba)S:Eu, (Ba,Sr,Ca)Ga$_2$S$_4$:Eu, K$_2$(Si,Ti,Ge)F$_6$:Mn, (Ca,Sr,Ba)$_5$(PO$_4$)$_3$(Cl,Br):Eu, and Ca$_5$(PO$_4$)$_3$Cl:Eu. In the case where the fluorescent member 50 contains the other phosphors, their content is appropriately adjusted so that the light-emitting properties of the present disclosure are obtained. The content of the other phosphors relative to the total amount of the phosphors contained is, for example, 5 mass % or less, preferably 3 mass % or less.

Resin Portion

The resin portion contained in the fluorescent member 50, for example, thermoplastic resins and thermosetting resins. Specific examples of thermosetting resins include epoxy resins, silicone resins, and modified silicone resins such as epoxy-modified silicone resins. Specific examples of thermoplastic resins include polyphthalamide resins and nylon-based resins.

Other Elements

The fluorescent member 50 may contain other elements in addition to the phosphors 70 and the resin. Examples of the other elements include light stabilizers, coloring agents, and fillers such as silica, barium titanate, titanium oxide, and aluminum oxide. When the fluorescent member contains the other elements, their content can be appropriately selected depending on the purpose. For example, in the case where a filler is contained as the other component, its content can be 0.01 parts by mass to 20 parts by mass relative to 100 parts by mass of the resin.

EXAMPLES

The following specifically describes examples of the present disclosure, but the examples do not limit the present disclosure.

Before producing the light-emitting device 100, the following first to fourth phosphors 71 to 74 were each provided.

As the first phosphor 71, a phosphor (hereinafter also referred to as "CCA") with a peak emission wavelength of about 460 nm having the composition represented by $Ca_5(PO_4)_3Cl:Eu$ was provided.

As the second phosphor 72, a phosphor (hereinafter also referred to as "chlorosilicate") with a peak emission wavelength of about 515 nm having the composition represented by $Ca_8MgSi_4O_{16}Cl_2:Eu$ was provided.

As the third phosphor 73, a phosphor (hereinafter also referred to as "YAG") with a peak emission wavelength of about 544 nm having the composition represented by $Y_3Al_5O_{12}:Ce$ was provided.

As the fourth phosphor 74, a phosphor (hereinafter also referred to as "SCASN") with a peak emission wavelength of about 635 nm having the composition represented by $(Sr,Ca)AlSiN_3:Eu$ was provided.

As the light-emitting elements 10, LEDs with a peak emission wavelength of about 405 nm were provided.

Example 1

Production of Light-Emitting Device

The light-emitting elements 10 that were the LEDs with a peak emission wavelength of about 405 nm, the first phosphor 71 (CCA), the second phosphor 72 (chlorosilicate), the third phosphor 73 (YAG), and the fourth phosphor 74 (SCASN) were combined to produce a light-emitting device in Example 1. The light-emitting device in Example 1 includes two light-emitting elements 10 as shown in FIG. 3. Both of the two light-emitting elements are LEDs with a peak emission wavelength of about 405 nm.

The content of the first phosphor 71 relative to the total amount of the phosphors is 15.3 mass % in the light-emitting device in Example 1. The content of the second phosphor 72 relative to the total amount of the phosphors is 42.1 mass %. The content of the third phosphor 73 relative to the total amount of the phosphors is 13.0 mass %. The content of the fourth phosphor 74 relative to the total amount of the phosphors is 29.6 mass %. The phosphors 70 blended so that the correlated color temperature was about 3500 K were added to a silicone resin and dispersed by mixing, and air in the mixture was removed to obtain a phosphor-containing resin composite. The phosphor-containing resin composite was injected and charged on the light-emitting elements 10 and was cured by heat. The light-emitting device in Example 1 was produced through the above steps.

Comparative Example 1

A light-emitting device in Comparative Example 1 was produced in substantially the same manner as Example 1 except that a combination of the second phosphor 72 (chlorosilicate), the third phosphor 73 (YAG), and the fourth phosphor 74 (SCASN) was used as the phosphors 70 without using the first phosphor 71 (CCA).

The content of the second phosphor 72 relative to the amount of the phosphors is 48.3 mass % in the light-emitting device in Comparative Example 1. The content of the third phosphor 73 relative to the total amount of the phosphors is 22.3 mass %. The content of the fourth phosphor 74 relative to the total amount of the phosphors is 29.4 mass %. The phosphors have been blended so that the correlated color temperature is about 3500 K.

Figure 8:
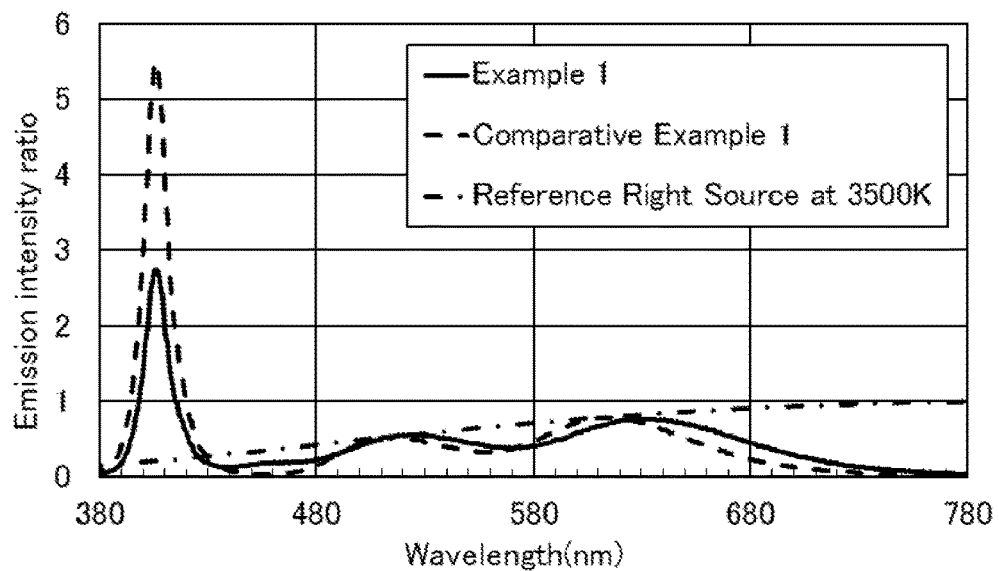
FIG. 8 shows the emission spectra of Example 1 and Comparative Example 1.
Figure 9:
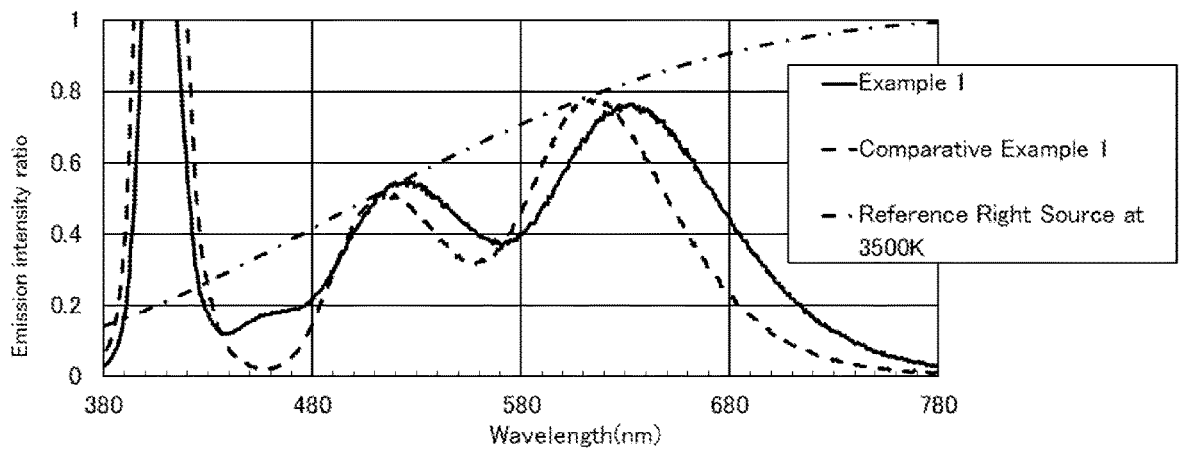
FIG. 9 shows the emission spectra of Example 1 and Comparative Example 1.

Because the light-emitting device in Example 1 contains the first phosphor, the emission spectrum is close to the spectrum of the reference light source in the range of 440 nm to 470 nm as shown in FIG. 8 and FIG. 9. This enables the light-emitting device in Example 1 to have good color rendering properties.

The R12 of the light-emitting device in Comparative Example 1 containing no first phosphor 71 was 6, and the R12 of the light-emitting device in Example 1 containing the first phosphor 71 was 56. Containing the first phosphor 71 in the light emitting device increased the value of the R12 and improved the color rendering properties of the light-emitting device.

The third phosphor 73 in the light-emitting device in Example 1 is also excited by the light emitted by the first phosphor 71. Hence, the emission intensity of the light-emitting device in Example 1 is higher than the emission intensity of the light-emitting device in Comparative Example 1 at about 544 nm, which is the peak emission wavelength of the third phosphor 73. Because the light-emitting device contains the first phosphor and the third phosphor, its emission spectrum is close to the spectrum of the reference light source, so that the light-emitting device in Example 1 can achieve good color rendering properties.

The light-emitting device according to the present disclosure can be used for apparatuses employing light-emitting diodes as excitation light sources and having good light-emitting properties, such as lighting apparatuses, LED displays, flashes for cameras, and backlights for liquid-crystal displays. In particular, the device can suitably be applied for lighting used in medical field and lighting used for irradiating food that are required to have high color rendering properties and to alleviate proliferation of germs.

The invention claimed is:

1. A light-emitting device comprising:
a light-emitting element with a peak emission wavelength in a range of 400 nm to 410 nm; and
a plurality of phosphors,
wherein the plurality of phosphors comprises:
a first phosphor excited by light emitted from the light-emitting element and having a peak emission wavelength in a range of 440 nm to 470 nm;
a second phosphor excited by the light emitted from the light-emitting element and having a peak emission wavelength in a range of 500 nm to 530 nm;
a third phosphor excited by the light emitted from the light-emitting element and having a peak emission wavelength in a range of 530 nm to 600 nm; and
a fourth phosphor excited by the light emitted from the light-emitting element and having a peak emission wavelength in a range of 600 nm to 660 nm, and
wherein the light-emitting device emits light with a mixed color comprising light emitted from the light-emitting element, fluorescence emitted from the first phosphor, fluorescence emitted from the second phosphor, fluorescence emitted from the third phosphor and fluorescence emitted from the fourth phosphor, and wherein the light with the mixed color has a continuous emission spectrum.

2. The light-emitting device according to claim 1, wherein the first phosphor comprises a Eu-activated alkaline-earth phosphate that contains Cl.

3. The light-emitting device according to claim 1, wherein the second phosphor comprises a Eu-activated halogen-containing alkaline-earth silicate.

4. The light-emitting device according to claim 1, wherein the third phosphor comprises a Ce-activated rare-earth aluminate.

5. The light-emitting device according to claim 1, wherein the fourth phosphor comprises a Eu-activated silicon nitride comprising Al and at least one of Sr and Ca.

6. The light-emitting device according to claim 2, wherein the first phosphor comprises an alkaline-earth phosphate having a composition represented by a formula of $(Ca,Sr,Ba)_5(PO_4)_3(Cl,Br):Eu$.

7. The light-emitting device according to claim 3, wherein the second phosphor comprises a halogen-containing alkaline-earth silicate having a composition represented by a formula of $(Ca,Sr,Ba)_8MgSi_4O_{16}(F,Cl,Br)_2:Eu$.

8. The light-emitting device according to claim 4, wherein the third phosphor comprises a rare-earth aluminate having a composition represented by a formula of $(Y,Lu,Gd)_3(Al,Ga)_5O_{12}:Ce$.

9. The light-emitting device according to claim 5, wherein the fourth phosphor comprises a silicon nitride having a composition represented by a formula of $(Sr,Ca)AlSiN_3:Eu$.

10. The light-emitting device according to claim 1, wherein a content of the first phosphor relative to a total amount of the plurality of phosphors is in a range of 5 mass % to 30 mass %.

11. The light-emitting device according to claim 1, wherein a content ratio of the first phosphor to the fourth phosphor is in a range of 0.2 to 1.2.

12. The light-emitting device according to claim 1, wherein a content ratio of the second phosphor to the fourth phosphor is in a range of 0.8 to 2.5.

13. The light-emitting device according to claim 1, wherein a content ratio of the third phosphor to the fourth phosphor is in a range of 0.4 to 2.5.

14. The light-emitting device according to claim 1, wherein the third phosphor can be efficiently excited by light emitted from the first phosphor.

15. The light-emitting device according to claim 1, wherein particles of the first phosphor, particles of the second phosphor, particles of the third phosphor, and particles of the fourth phosphor each have a size in a range of 5 μm to 50 μm.

16. The light-emitting device according to claim 1, wherein a maximum emission intensity of the light-emitting device in a wavelength range of 600 nm to 660 nm is 1.5 to 10 times as large as a maximum emission intensity of the light-emitting device in a wavelength range of 440 nm to 470 nm.

17. The light-emitting device according to claim 1, wherein a maximum emission intensity of the light-emitting device in a wavelength range of 600 nm to 660 nm is 1 to 2 times as large as a maximum emission intensity of the light-emitting device in a wavelength range of 500 nm to 530 nm.

18. The light-emitting device according to claim 1, wherein an amount of energy of the light-emitting device per unit time in a range of 400 nm to 410 nm is in a range of 10 mW to 60 mW.

19. A light-emitting device comprising:
a light-emitting element with a peak emission wavelength in a range of 400 nm to 410 nm; and
a fluorescent member comprising:
  a first phosphor with a peak emission wavelength in a range of 440 nm to 470 nm comprising a Eu-activated alkaline-earth phosphate that contains Cl;
  a second phosphor with a peak emission wavelength in a range of 500 nm to 530 nm comprising a Eu-activated halogen-containing alkaline-earth silicate;
  a third phosphor with a peak emission wavelength in a range of 530 nm to 600 nm comprising a Ce-activated rare-earth aluminate; and
  a fourth phosphor with a peak emission wavelength in a range of 600 nm to 660 nm comprising a Eu-activated silicon nitride comprising Al and at least one of Sr and Ca,
wherein a half-width in an emission spectrum of the first phosphor is in a range of 29 nm to 49 nm.

* * * * *